(12) United States Patent
Gengrinovitch

(10) Patent No.: US 8,435,800 B2
(45) Date of Patent: May 7, 2013

(54) ACTIVATED LABELING REAGENTS AND METHODS FOR PREPARING AND USING THE SAME

(75) Inventor: Stela Gengrinovitch, Kfar Hanania (IL)

(73) Assignee: BioSight Ltd., Carmiel (IL)

( * ) Notice: Subject to any disclaimer, the term of this patent is extended or adjusted under 35 U.S.C. 154(b) by 958 days.

(21) Appl. No.: 11/719,616

(22) PCT Filed: Nov. 22, 2005

(86) PCT No.: PCT/IL2005/001238
§ 371 (c)(1),
(2), (4) Date: Mar. 19, 2009

(87) PCT Pub. No.: WO2006/054310
PCT Pub. Date: Mar. 26, 2006

(65) Prior Publication Data
US 2009/0203879 A1   Aug. 13, 2009

Related U.S. Application Data

(60) Provisional application No. 60/629,582, filed on Nov. 22, 2004.

(51) Int. Cl.
*C07D 311/88* (2006.01)
*C07H 19/00* (2006.01)
*C07K 1/113* (2006.01)
*G01N 21/76* (2006.01)

(52) U.S. Cl.
USPC ........... 436/166; 436/172; 436/800; 530/345; 530/405; 530/409; 536/25.32; 549/227

(58) Field of Classification Search .................. None
See application file for complete search history.

(56) References Cited

U.S. PATENT DOCUMENTS

| | | | |
|---|---|---|---|
| 4,738,920 A | 4/1988 | Ishiguro | 435/6 |
| 5,324,833 A | 6/1994 | Sieber et al. | 544/183 |
| 5,521,319 A | 5/1996 | Huber et al. | 548/304.1 |
| 5,532,379 A | 7/1996 | Fujimoto | 548/304.1 |
| 5,538,001 A | 7/1996 | Bridges | 128/206.24 |
| 5,583,001 A | 12/1996 | Bobrow et al. | 435/7.5 |
| 5,601,977 A | 2/1997 | Akhavan-Tafti et al. | 435/6 |
| 5,789,588 A | 8/1998 | Takenishi et al. | 544/130 |
| 5,892,057 A | 4/1999 | Wilkes et al. | 548/547 |

(Continued)

FOREIGN PATENT DOCUMENTS
WO   WO 89/03849   5/1989

OTHER PUBLICATIONS

Adamczyk et al. Preparation of Succinimidyl and Pentafluorophenyl Active Esters . . . Bioconjugate Chemistry. 1997, vol. 8, No. 2, pp. 253-255.*

(Continued)

*Primary Examiner* — Jeffrey E Russel
(74) *Attorney, Agent, or Firm* — Winston & Strawn LLP

(57) ABSTRACT

The present invention relates in general to labeling reagents useful for labeling biomolecules. In particular, the invention provides activated labeling reagents having the formula L-Ph, wherein L is an activated labeling molecule and Ph is a phenol. The invention further provides methods of preparing the labeling reagents, methods of using the labeling reagents for synthesizing a labeled biomolecule, kits that include reagents for labeling a biomolecule and kits containing labeled biomolecules.

5 Claims, 11 Drawing Sheets

U.S. PATENT DOCUMENTS

| | | | |
|---|---|---|---|
| 6,057,096 | A | 5/2000 | Rothschild et al. ............... 435/6 |
| 6,080,839 | A | 6/2000 | Takalo et al. ................. 530/334 |
| 6,407,263 | B1 | 6/2002 | Wilkes et al. ................. 548/547 |
| 6,670,194 | B1 | 12/2003 | Aebersold et al. ............ 436/173 |
| 6,809,186 | B1 | 10/2004 | Morseman et al. ........... 530/409 |
| 2003/0059537 | A1* | 3/2003 | Chilkoti et al. ............... 427/256 |
| 2003/0170766 | A1* | 9/2003 | Brown et al. .................... 435/15 |
| 2004/0038294 | A1* | 2/2004 | Evangelista et al. ........... 435/7.1 |
| 2005/0159606 | A1* | 7/2005 | Lukhtanov .................... 549/223 |

OTHER PUBLICATIONS

Gee et al. 4-Sulfotetrafluorophenyl (STP) Esters: New Water-Soluble Amine-Reactive Reagents for Labeling Biomolecules. Tetrahedron Letters. 1999, vol. 40, pp. 1471-1474.*

Lefevre et al. Texas Red-X and Rhodamine Red-X, New Derivatives of Sulforhodamine 101 . . . Bioconjugate Chemistry. 1996, vol. 7, No. 4, pp. 482-489.*

Database EPDOC European Patent Office, The Hague, NL; XP002525534, HU-198057 "Process for producing Biotin-Pentafluorophenyl Esters, Process for producing Pentafluorphenol derivatives of biotin", (Jan. 30, 1989).

Korshun, Vladimir A et al., "Reagents for multiple non-radioactive labeling of oligonucleotides", Synthetic Communications 1996; 26(13):2531-47.

Somlai Csaba et al., "Synthesis and use of pentafluorophenyl 6-(biotinylamido) hexanoate an alternative reagent for labeling of proteins with biotin moiety", Zeitschrift fur naturforschung, Teil B: Anorganische Chemie, Organishe Chemie, Verlag Der Zeitschrift fur Naturforschung. Tubingen, DE 1993; 48(4):511-6.

Tong G, et al., "The synthesis of oligonucleotide-polyamide conjugate molecules suitable as PCR primers", J. Org Chem 1993; 58(8):2223-2231.

Supplementary European search report Apr. 27, 2009 (EP 05809162.0).

International Search Report PCT/IL2005/01238, (Apr. 21, 2006).

* cited by examiner

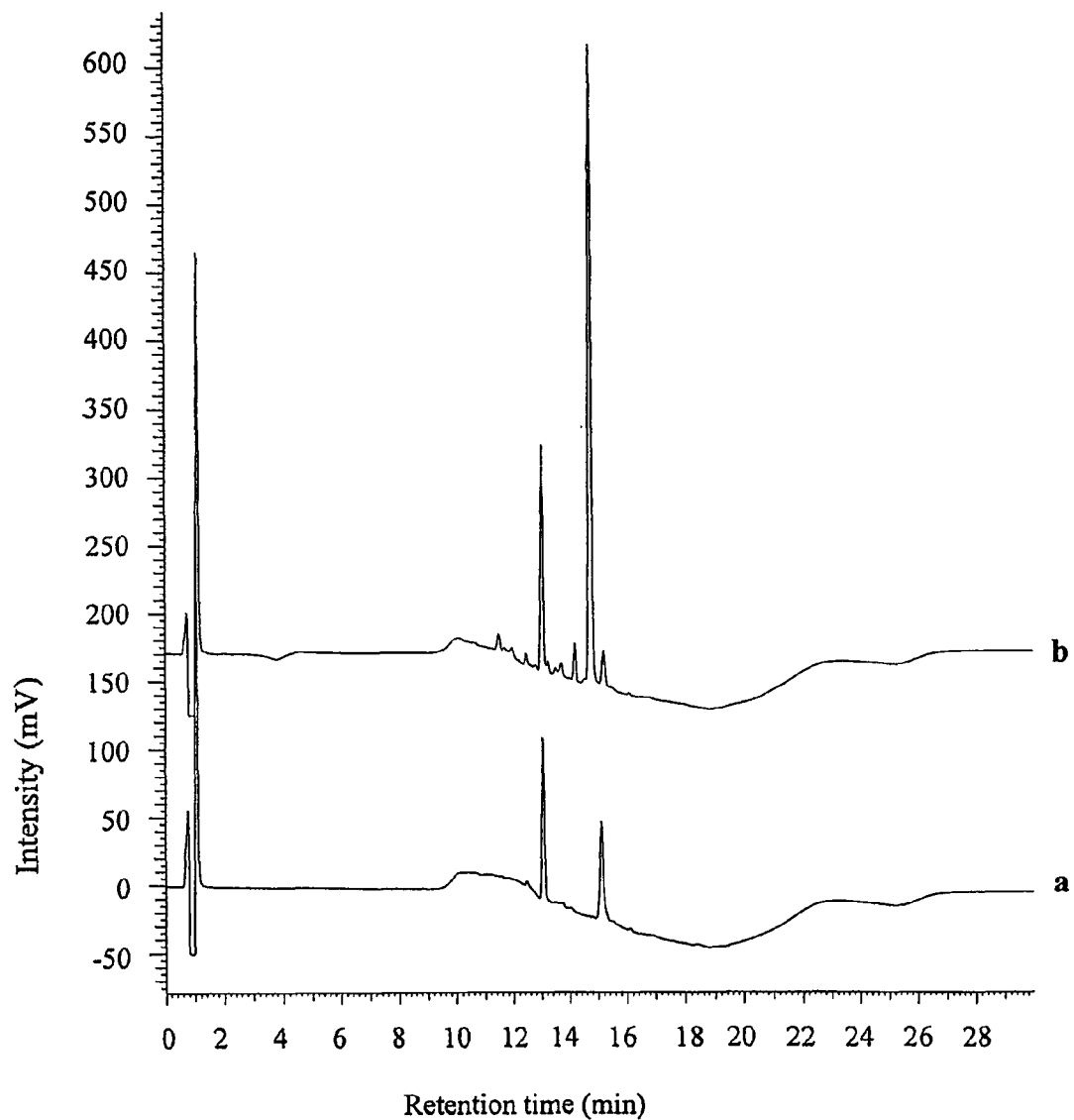

SEQUENCE LISTING

```
<160> NUMBER OF SEQ ID NOS: 1

<210> SEQ ID NO 1
<211> LENGTH: 21
<212> TYPE: PRT
<213> ORGANISM: Mus musculus

<400> SEQUENCE: 1

Met Glu Val Gly Trp Tyr Arg Pro Pro Phe Ser Arg Val Val His Leu
1               5                   10                  15

Tyr Arg Asn Gly Lys
            20
```

ACTIVATED LABELING REAGENTS AND METHODS FOR PREPARING AND USING THE SAME

This application is a 371 filing of International Patent Application No. PCT/IL2005/001238, filed Nov. 22, 2005, which claims priority to U.S. Provisional Application No. 60/629,582, filed Nov. 22, 2004.

FIELD OF THE INVENTION

The present invention relates in general to the field of labeling reagents and in particular to activated labeling reagents that are able to covalently bind to biomolecules and to methods of use thereof. The invention further provides methods of preparing the activated labeling reagents, methods of using the labeling reagents for synthesizing a labeled biomolecule, kits for labeling a biomolecule and kits containing labeled biomolecules.

BACKGROUND OF THE INVENTION

Labeling of Biomolecules

Chemical modification of biomolecules is well known in the art. Reagents and methods useful for the covalent attachment of labels, tags and reporter molecules to biomolecules have provided valuable tools in the fields of biochemistry, molecular biology and diagnostics. Labeled biomolecules are useful for inter alia detecting target components in biological samples and isolating a target molecule.

Non-isotopic labels are generally preferred since they are safer to handle, less toxic to the user and the environment and are easier to store than radioactive labels. In addition, some of the commonly employed isotopic labels have relatively short half-lives. The preparation of non-isotopic labeled biomolecules, including oligonucleotides, peptides, proteins, lipids and sugars, is known in the art and there exists an abundance of commercially available kits useful for the preparation of such labeled biomolecules.

There are various types of non-isotopic labels useful for labeling biomolecules. One type of label is chemically bound to the biomolecule and serves as a direct means for identification and localization. One non-limiting example of this type is a fluorochrome or fluorophore moiety, which upon exposure to appropriate light wavelengths becomes excited into a high-energy state and emits fluorescent light. Another example is a moiety detectable by electron microscopy (EM), for example a gold label.

A second type of label for a biomolecule utilizes a chemical reagent, which undergoes a change when exposed to the proper reactants. One example of the second type is an enzyme, which can produce a colored product when exposed to a specific enzyme substrate. The chromogenic product identifies the presence and/or position of the labeled biomolecule.

Another type of label utilizes specific binding entities, including the biotin-avidin/streptavidin system. The biomolecule is preferably linked to biotin and an avidin (or streptavidin) conjugated fluorochrome or enzyme is used for detection of the biotin label. The specific binding affinity between the biotin and the avidin (or streptavidin) conjugate provides the specificity for attaching the fluorochrome, enzyme or EM marker to the biomolecule.

Derivatives of Labeling Molecules

Certain derivatives of labeling molecules are useful in various applications in order to enable, for example a simpler labeling process or retrieval of an unlabeled biomolecule following identification and isolation.

N-hydroxysulfosuccinimide (NHS) esters provide one of the most common activation chemistries for creating reactive acylating agents. Sulfo-N-hydroxy succinimides (often referred to as S—NHS), including the acid and salt counterparts, have a wide range of utility in commercial areas, including but not limited to reagents for the manufacture of biotin conjugates.

Conjugation of biotin to protein can be performed using several methods, for example the free amino group of the protein maybe reacted with an N-hydroxysuccinimide ester of biotin (Jasiewicz, M. L. et al., Exp. Cell. Res., 100:213, 1976). Reisfeld et al., teaches nonradioactive hybridization probes prepared by the reaction of biotin hydrazide derivatives (BBRC, 142:519, 1987). Shiga et al., has disclosed the synthesis of a novel biotin derivative having a diazo group as the reactive site (Anal. Sci., 9:553, 1993).

U.S. Pat. No. 5,521,319 relates to a N-hydroxysuccinimide activated biotinylation reagent having a broader solubility spectrum in both polar and non-polar solvents than those biotinylated reagents previously known.

U.S. Pat. No. 5,532,379 teaches trifunctional compounds containing the biotin moiety, the N-hydroxysuccinimido active ester (NHS), and the photoactivatable aryl azide. The compounds are cleavable and generally useful in applications utilizing biotin, and particularly the avidin-biotin complex.

U.S. Pat. No. 5,789,588 discloses a novel biotin group-containing carbodiimide derivative useful as a reagent for labeling a nucleic acid or a protein.

U.S. Pat. No. 6,057,096 teaches bioreactive agents comprising a detectable moiety bound to a photocleavable moiety useful for conjugating to biological molecules such as nucleic acids, proteins, lipids and cytokines. Conjugates comprising the bioreactive agent and a biomolecule can be selectively cleaved using electromagnetic radiation. In certain embodiments the detectable moiety is selected from biotin, coumarin, dansyl, rhodamines, fluoresceins, dinitrophenyl, and combinations thereof.

U.S. Pat. No. 6,670,194 teaches analytical reagents and mass spectrometry-based methods using the reagents for the quantitative analysis of protein expression or protein function in mixtures of proteins. The methods employ affinity labeled protein reactive reagents having three portions: an affinity label (A) covalently linked to a protein reactive group (PRG) through a differentially labeled isotopic linker group (L). In certain embodiments the affinity label is selected from biotin or a modified biotin. According to that disclosure the affinity label functions as a molecular handle to bind to a capture reagent or target. In one embodiment PRG is selected from an amine reactive pentafluorophenyl ester group, an amine reactive N-hydroxy succinimide ester group, a sulfonyl halide, an isocyanate, an isothiocyanate, an active ester, a tetrafluorophenyl ester, an acid halide, an acid anhydride, a homoserine lactone-reactive primary amine group, a carboxylic acid reactive amine, alcohols, and 2,3,5,6-tetrafluorophenyl trifluoroacetate. A biotin 2,3,5,6-tetrafluorophenyl ester was shown to be an intermediate in the synthesis of an analytical reagent for identifying GM1-gangliosidosis.

U.S. Pat. No. 5,324,833 teaches the use of pentafluorophenol activated esters useful for the pre-activation of Fmoc-amino acids such as Fmoc-Asn-OH and Fmoc-Gln-OH, which are difficult to incorporate in solid phase peptide synthesis. The patent neither teaches nor suggests the use of pentafluorophenol for activating a labeling moiety.

U.S. Pat. No. 6,809,186 is directed to simplified methods for coupling labels to particular target moieties using NHS chemistry. In those methods, all reactants are prepared separately then combined in such a way that they do not react with each other until the targeted compound is added to activate the cross-linking chemicals. In one embodiment the method of conjugating a label to a target moiety, comprises: (a) placing a label, NHS, and a carbodiimide in a container such that the three components are sequestered from reaction with each other; (b) storing the components in dry form; and (c) hydrating the components to initiate reaction between them, wherein a target is added at the time the components are hydrated and the target is subsequently conjugated to the label.

U.S. Pat. Nos. 5,892,057 and 6,407,263 disclose water-soluble reagents with a wide range of applications, including as biotin conjugates. While these activated forms (NSH, S—NSH) are useful for labeling macromolecules such as proteins and antibodies, they are inefficient for the labeling of small molecules such as peptides, hence creating the need for more efficient activated labels.

Baumeister et al., (Int. J. Pep. Res. Therap. Vol. 11:139, 2005), teach the use of a biotin-ONp derivative useful in solid phase peptide synthesis.

Several types of kits comprising activated biotin derivatives are commercially available, including the EZ-LINK™ reagents that couple biotin, enzymes or fluorophores to cysteine or lysine residues (Pierce), the ULS® Universal linkage System labeling kits for the labeling of nucleic acids (Fermentas) and the DSB-X™ (desthiobiotin) kits for protein labeling (Molecular Probes). Those kits use N-hydroxysuccinimide or sulfo-N-hydroxysuccinimide as the activated reagent.

There is a clear need for reagents adapted to provide efficient labeling of diverse biomolecules, including small peptides, useful for different applications. The above references neither teach nor suggest phenyl ester activated derivatives of a labeling molecule for the efficient labeling of biomolecules.

SUMMARY OF THE INVENTION

The present invention provides stable and efficient activated labeling reagents that are able to react with primary amines. The reagents are simple to prepare, and provide high yields of labeled biomolecules. In addition, the activated labeling reagents are versatile and may be used to efficiently label a wide variety of biomolecules including proteins, peptides, nucleotides, nucleic acids, lipids and sugars.

According to one aspect the present invention provides an activated labeling reagent useful for the labeling of biomolecules wherein the activated labeling reagent has the formula L-Ph wherein L is an activated labeling molecule suitable for labeling of biomolecules and Ph is a phenol.

According to certain embodiments, L maybe any labeling molecule, labeling tag, reporter enzyme or substrate of a reporter enzyme that upon activation is able to bind to a biomolecule. According to one embodiment L is a labeling molecule selected from biotin, a biotin derivative, a fluorophore, a hapten, a reporter enzyme, the substrate of a reporter enzyme and a chemical moiety. According to some embodiments the biotin analogues and derivatives are selected from desthiobiotin, iminobiotin, actithiazic acid, 5-(2-thienyl)valeric acid, dehydrobiotin and biotinsilane. The labeling molecules are preferably active esters of said molecules.

According to one preferred embodiment L is selected from the group consisting of biotin and a biotin derivative.

In certain embodiments a fluorophore is selected from alizarin complexone, 5-(3-Nitrophenylazo) salicylic acid, aurintricarboxylic acid, carminic acid, chrome azurol S, chromoxane cyanine R, chrysoidin, DABCYL, DANCYL, dinitrophenyl amino acid derivative, 4',5'-Dibromofluorescein, diiodofluorescein, eosin B, Eosin Y, erytrosin B, fluorescein, fluoresceinamine, fluorexon, gallocyanine, HABA, 3-hydroxy-4-(2-hydroxy-4-sulfo-1-naphthylazo)-2-naphthalenecarboxylic acid, 7-methoxycoumarin-4-acetic acid (MCA), merbromin, methyl red, mordant orange 1, mordant orange 6, Mordant orange 10, Mordant yellow 7 (3-methyl-5-(4-sulfophenylazo)salicylic acid), Mordant yellow 10 (5-(4-sulfophenylazo)salicylic acid), mordant yellow 12 (5-(4-aminophenylazo)salicylic acid), naphthochrome green, phloxine B, rhodamine B, rose Bengal, 4,5,6,7-tetrachlorofluorescein, 3',3",5',5"-tetraiodophenolphathalein, Violamine R, Zincon and derivatives thereof.

According to one preferred embodiment L is selected from the group consisting of fluorescein and rhodamine.

In certain embodiments Ph is selected from fluoro-phenol, chloro-phenol, iodo-phenol, thio-phenol, bromo-phenol, hydroxy-phenol, alkoxy-phenol, nitro-phenol, sulfo-phenol, hydroxyl-naphthalene derivatives, and combinations and salts thereof. In one preferred embodiment Ph is pentafluorophenol.

In certain embodiments the biomolecule is selected from a protein, a peptide, a nucleic acid molecule, a sugar and a lipid.

According to another aspect the present invention provides an activated labeling reagent useful for the labeling of a biomolecule wherein the activated labeling reagent has the formula L-Sp-Ph wherein L is an activated labeling molecule suitable for labeling of a biomolecule, Sp is a spacer molecule that links L to Ph, and Ph is a phenol.

According to one embodiment L is an activated labeling molecule selected from activated biotin, an activated biotin derivative, an activated fluorophore, an activated reporter enzyme and an activated chemical moiety.

According to some embodiments the biotin analogues and derivatives are selected from desthiobiotin, iminobiotin, actithiazic acid, 5-(2-thienyl)valeric acid, dehydrobiotin and biotinsilane.

According to one preferred embodiment L is an active ester of biotin. In another preferred embodiment L is an active ester of a biotin derivative.

In certain embodiments a fluorophore is selected from alizarin complexone, 5-(3-Nitrophenylazo) salicylic acid, aurintricarboxylic acid, carminic acid, chrome azurol S, chromoxane cyanine R, chrysoidin, DABCYL, DANCYL, dinitrophenyl amino acid 4',5'-Dibromofluorescein, diiodofluorescein, Eosin B, Eosin Y, erytrosin B, fluorescein, fluoresceinamine, fluorexon, gallocyanine, HABA, 3-hydroxy-4-(2-hydroxy-4-sulfo-1-naphthylazo)-2-naphthalenecarboxylic acid, MCA, merbromin, methyl red, mordant orange 1, mordant orange 6, mordant orange 10, mordant yellow 7 (3-methyl-5-(4-sulfophenylazo)salicylic acid), mordant yellow 10 (5-(4-sulfophenylazo)salicylic acid), mordant yellow 12 (5-(4-aminophenylazo)salicylic acid), naphthochrome green, phloxine B, rhodamine B, rose Bengal, 4,5,6, 7-Tetrachlorofluorescein, 3',3",5',5"-tetraiodophenolphathalein, violamine R, zincon and derivatives thereof.

According to one preferred embodiment L is fluorescein. In another preferred embodiment L is rhodamine According to certain embodiments Sp may be a natural or a synthetic molecule. In certain embodiments is selected from an amino acid, an amino acid derivative, a peptide, a peptidomimetic and a lipid. In other embodiments the spacer is selected from alpha-aminosuberic acid, homocitrulline, homoserine, hydroxyproline, 4-nitrophenylalanine, penicillamine, statine, beta-alanin, 6-aminohexanoic acid, and 4-aminobutyric acid, para-amino benzoic acid, 5-aminopentanoic acid, 4-aminophenylacetic acid and 4-(aminomethyl) benzoic acid. Preferably, the spacer is a beta amino acid such as 6-aminohexanoic acid (Ahx) or a short peptide of about 2 to about 10 residues of 6-aminohexanoic acids, for example a three-residue peptide Ahx-Ahx-Ahx.

In other embodiments the spacer is a lipid spacer selected from glutaric acid, adipic acid, pimelic acid, suberic acid, azelaic acid, sebacic acid, roccellic acid, 11-aminoundecanoic acid and 7-aminoheptanoic acid.

In other embodiments the spacer is selected from a non-cleavable spacer and a cleavable spacer that can be cleaved by chemical, enzymatic or photoreactive cleavage.

In yet other embodiments the spacer is a synthetic spacer selected from a non-cleavable spacer of amino polyethylene oxide carboxylic acid and a cleavable spacer with cleavable sulfo bond (S—S) having the general formula of $H_2N-R-S-S-R'-COOH$ (R, R'=$(CH_2)n$)

In certain embodiments Ph is selected from fluoro-phenol, chloro-phenol, iodo-phenol, thio-phenol, bromo-phenol, hydroxy-phenol, alkoxy-phenol, nitro-phenol sulfo-phenol, naphthalene, derivatives or salts thereof or combinations thereof. In certain embodiments Ph is selected from 2,4,5-trichlorophenol, pentachlorophenol, 2,4,5-triiodophenol, 2,4,5-tribromophenol, pentabromophenol, 2-nitrophenol, 3-nitrophenol, 4-nitrophenol, 2,4,5-trifluorophenol, and 2,4,5,6-tetrafluoro-3-methoxyphenol, tetrafluoro-resorcinol, 3-nitrophenol-5-sulfonic acid, 6-nitro-4-aminophenol-6-sulfonic acid, 8-hydroxy-5,7-dinitro-2-naphthalenesulfonic acid, and 2,4-dinitro-1-naphthol.

In one preferred embodiment Ph is pentafluorophenol.

In certain embodiments the biomolecule is selected from a protein, a peptide, a nucleic acid molecule, a sugar and a lipid.

According to another aspect, the present invention provides a method of labeling a biomolecule comprising the steps of:
 a) providing an active labeling reagent having the formula selected from L-Ph and L-Sp-Ph, wherein L is an activated labeling molecule suitable for labeling of a biomolecule, Sp is a spacer molecule that links L to Ph, and Ph is a phenol;
 b) providing a biomolecule having at least one functional group selected from an amine moiety, a thio moiety and a hydroxy moiety;
 c) exposing the active labeling reagent with the biomolecule under conditions to allow covalent binding between the reagent and biomolecule to provide a labeled biomolecule;
 d) precipitating said labeled biomolecule.

According to certain embodiments the method may further comprise the step of
 e) purifying said labeled biomolecule.

According to certain embodiments of the present invention the labeling method may be carried out under solid phase labeling conditions. According to other embodiments of the present invention the labeling method may be carried out under liquid phase labeling conditions.

According to yet another aspect, the present invention provides a kit comprising at least one activated labeling reagent for the labeling of a biomolecule, the activated labeling reagent having the formula selected from L-Ph and L-Sp-Ph, wherein L is an activated labeling molecule suitable for labeling of a biomolecule, Sp is a spacer molecule that links L to Ph, and Ph is a phenol; and instructions for use.

According to another aspect the present invention provides a kit comprising at least one labeled biomolecule, the labeled biomolecule prepared according to the method comprising the steps of:
 a) providing an active labeling reagent having the formula selected from the group consisting of L-Ph and L-Sp-Ph, wherein L is an activated labeling molecule suitable for labeling of a biomolecule, Sp is a spacer molecule that links L to Ph, and Ph is a phenol;
 b) providing a biomolecule having at least one functional group selected from an amine moiety, a thio moiety and a hydroxy moiety;
 c) exposing the active labeling reagent to the biomolecule under conditions to allow covalent binding between the reagent and biomolecule to provide a labeled biomolecule;
 d) precipitating said labeled biomolecule;
and instructions for use.

In some embodiments the present invention provides a kit useful for the labeling of a biomolecule comprising
 a) an activated labeling reagent having the formula selected from the group consisting of L-Ph and L-Sp-Ph;
 b) a reaction solution;
 c) a stop solution;
 d) a precipitation solution;
 e) a separation solution; and
 f) a separation gel.

BRIEF DESCRIPTION OF THE FIGURES

FIG. 1A shows the structure of d-biotin-O-PFP; FIG. 1B shows the structure of d-biotin-βAla-O-PFP; and FIG. 1C shows the structure of d-biotin-Ahx-O-PFP.

FIG. 2A shows the structure of d-biotin-Ahx-Ahx-O-PFP; and FIG. 2B shows the structure of d-biotin-2-aminoethyl-carboxymethyldisulfide-O-PFP.

FIG. 3A shows the structure of fluorescein-O-PFP. FIG. 3B shows the structure of rhodamine-O-PFP.

FIG. 8A shows HPLC analysis of free rhodamine (a) compared to rhodamine-O—PFP (b).

DETAILED DESCRIPTION OF THE INVENTION

Figure 1A:
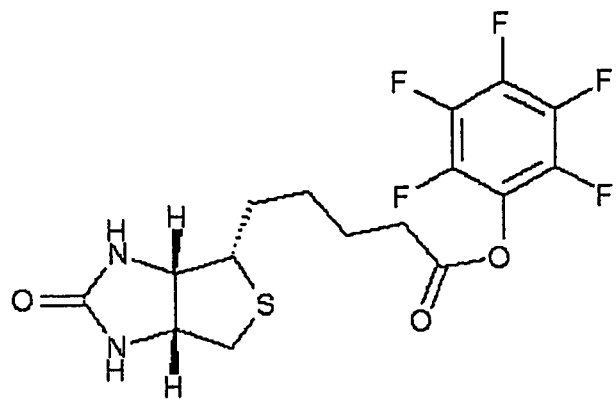
FIGS. 1A-1C illustrate molecular structures of certain activated labeling reagents of the invention.

Labeled or tagged biomolecules may be used in many applications including diagnostics, therapeutic and analytical methods. According to one aspect the present invention provides activated labeling reagents useful for the labeling or tagging of a wide variety of a biomolecule, including proteins, peptides, nucleic acids, lipids and sugars. The activated labeling reagents have attributes that make them particularly advantageous for use in the chemical, biological and medical laboratory. Among the advantageous properties of the activated labeling reagents of the invention:
  a. afford high yields of labeled biomolecule;
  b. versatile and allow labeling of a variety of biomolecules including proteins, peptides, nucleic acids, amino lipids and amino sugars;
  c. useful for labeling small peptides (from about 2 to about 40 amino acids);
  d. stable and may be stored for at least 24 hours in the reaction mixture and at least six months in solid phase;
  e. useful for both solid phase labeling and liquid phase labeling;
  f. the ester of labeling reagent reacts with amines to form a covalent amide bond between the labeling molecule and the biomolecule;
  g. the phenol is a good leaving group that does not continue to react after covalent bond formation;
  h. the linkage between the label moiety and the biomolecule is stable, with no significant loss of the label during storage Conjugates Biomolecules can be covalently coupled to other molecules or compounds useful for detection of the biomolecule in analytical, diagnostic and pharmaceutical applications. The combination of a biomolecule and another molecule or compound is generally referred to as a "conjugate." For example, a conjugate may be composed of nucleic acid or peptide and another molecule such as a labeling moiety (e.g., a fluorophore), a binding ligand (e.g., a biotin derivative) and an enzyme (e.g., alkaline phosphatase). These particular conjugates are useful in detecting the presence of the nucleic acid or peptide, binding or capturing it, and/or identifying its binding target.

Effective conjugation of a compound, such as an enzyme, biotin or a fluorescent dye, to a biological molecule generally requires that the resulting labeled conjugate retain the bioactivity of the biological molecule. A conjugate may have only limited utility if, upon coupling, the functional activity of the biological molecule is diminished or lost.

Conjugates are prepared by covalently coupling the conjugate components. The coupling may or may not involve the use of a linker compound or molecule, which serves to join the conjugate components. The usefulness of the conjugate is generally limited by the stability of the linkage between the conjugate components thus a linker is typically chosen to provide a stable coupling between the two components.

"Activated labeling reagent" as used herein refers to a labeling molecule linked to a phenol via the hydroxy moiety of phenol to form an ester; i.e. L-C(O)—O-Ph. In some embodiments a spacer, Sp, is incorporated providing a reagent having the structure L-Sp-C(O)—O-Ph.

d-Biotin d-biotin is an example of a class of molecules useful for preparing conjugates. d-biotin (Vitamin H) is naturally occurring and has an extremely high binding affinity ($Kd\sim 10^{-15}$) for avidin and streptavidin. Because of the affinity of biotin for avidin, biotin-containing conjugates have been widely used in bioanalytical procedures including immunoassays, affinity chromatography, immunocytochemistry, and nucleic acid hybridization (Green, Adv. Protein Chem. 29:85, 1975; Wilchek and Bayer, Anal. Biochem. 171:1, 1988; Wilchek and Bayer, Meth. Enzymol. 184:5, 1990).

In the above assays biotin is typically covalently coupled to one of the assay components, including proteins, such as antibodies, antibody fragments, enzymes and hormones; peptides; nucleic acids such as oligonucleotides and a nucleic acid probes; lipids; sugars and smaller molecules such as drugs or other similar compounds. In certain applications biotin may be coupled to a solid phase or support.

The covalent coupling of biotin to another molecule involves bond formation through a chemical reaction between suitable chemical functional groups. A reactive biotin derivative is typically used for the coupling of biotin to a molecule such as a nucleic acid or peptide. Reactive biotin derivatives for conjugation may readily be prepared from biotin, and are typically carboxylic acid derivatives or, in some cases, nucleophilic derivatives such as amine or hydrazide derivatives. Common reactive biotin derivatives include reactive biotin esters such as an N-hydroxysuccinimide (NHS) ester. For example, biotin NHS esters may be conveniently attached to proteins and peptides through a free amino group, such as the ϵ-amino group on lysine residues. Other reactive biotin derivatives include nucleophilic derivatives, such as biotin hydrazide, which may be conjugated to glycoproteins through aldehyde groups generated by oxidation of their carbohydrate groups. Reactive biotin derivatives are commercially available. Many of these biotin derivatives contain various chemical groups between the biotin moiety and the reactive group.

The present invention is meant to include biotin and biotin derivatives. Certain biotin analogues and derivatives include in a non-limiting manner desthiobiotin, iminobiotin, actithiazic acid, 5-(2-thienyl)valeric acid, dehydrobiotin and biotinsilane.

Fluorophores

Common labeling compounds include fluorescent dyes, such as fluorescein and rhodamine, and examples of ligands for binding to their binding partners include drug compounds such as digoxigenin. Like biotin, these compounds are generally derivatized to contain functional groups that react readily with the biological molecule. For example, fluorescein isothiocyanate is a reactive fluorescein derivative that may readily be conjugated to proteins through their sulfhydryl groups. Other non-limiting examples of fluorophores useful in carrying out the invention include dibenzopyrrometheneboron difluoride dyes as disclosed in U.S. Pat. No. 5,433,896. Other fluorophores useful for activation by the activating reagents of the present invention include alizarin complexone, 5-(3-nitrophenylazo)salicylic acid (alizarin yellow GG), aurintricarboxylic acid, 5-carboxyfluorescein, 6-carboxyfluorescein, 5-carboxyrhodamine, 6-carboxyrhodamine, carminic acid (Natural red 4), chrome azurol S (Mordant Blue 29), chromoxane cyanine R (Mordant Blue 3), chrysoidin (Basic Orange 2), 4',5'-Dibromofluorescein (Solvent red 72), 7-diethylaminocoumarin-4-acetic acid (DMACA), diiodofluorescein (Solvent red 73), 5-dimethylaminonaphtalen-1-sulfonyl-N-hexanoic acid (Dansyl-X), dinitrophenyl amino acid (Dinitrophenyl-N-Alanine), Eosin B (Acid red 91), Eosin Y (Solvent red 43), erytrosin B (Acid red 51, 2',4',5',7'-Tetraiodofluorescein), Fluorescein (Solvent yellow 94), fluoresceinamine (4-aminofluorescein), 6-(Fluorescein-5-carboxyamido)-hexanoic acid, fluorexon (Bis[N,N-bis(carboxymethyl)aminomethyl]fluorescein), Gallocyanine (Mordant Blue 10), HABA (2-(4-hydroxyphenylazo)

benzoic acid), 3-hydroxy-4-(2-hydroxy-4-sulfo-1-naphthylazo)-2-naphthatenecarboxylic acid (calconcarboxylic acid), MCA (7-methoxycoumarin-3-carboxylic acid), merbromin (Mercurochrome), methyl red (Acid red 2), mordant orange 1 (Alizarin yellow R), mordant orange 6, mordant orange 10, mordant yellow 7 (3-methyl-5-(4-sulfophenylazo)salicylic acid), mordant yellow 10 (5-(4-sulfophenylazo)salicylic acid), mordant yellow 12 (5-(4-aminophenylazo)salicylic acid), naphthochrome green (Mordant green 31), phloxine B (Acid red 92), 1-pyreneacetic acid, 1-pyrenebutanoic acid, rhodamine B (Basic violet 10), Rose Bengal (Acid red 94), 4,5,6,7-tetrachlorofluorescein, 3',3",5',5"-tetraiodophenolphathalein, violamine R (Acid violet 9), zincon (2-[1-(2-hydroxy-5-sulfophenyl)-3-phenyl-5-formazano]benzoic acid) (Floyd J. Green., The Sigma-Aldrich Handbook of Stains, Dyes and Indicators., 1991)

Reporter Enzymes and Substrates

According to other embodiments of the present invention, L is a detectable reporter enzyme or a substrate of a reporter enzyme. Enzymes including beta-galactosidase, beta-glucuronidase, luciferase or green fluorescent protein (GFP), RFP, YFP alkaline phosphatase, carboxyl esterase, and horseradish peroxidase. Examples of reporter enzyme substrates include BCIP (5-bromo-4-chloro-3-indoxyl phosphate) and NBT (Nitro blue tetrazolium), which are substrates for alkaline phosphatase; X-Gal (5-bromo-4-chloro-3-indolyl-beta-galactopyranoside), which is a substrate for beta-galactosidase; X-GlcU (5-bromo-4-chloro-3-indolyl-beta-D-glucuronide), which is a substrate for beta-glucuronidase; XTT (2,3-bis-(2-methoxy-4-nitro-5-sulfophenyl)-2H-tetrazolium-5-carboxanilide), which is a substrate for redox enzymes; and D-luciferin, which is a substrate for luciferase.

According to one embodiment the substrate labeled biomolecule is detectable by a reporter enzyme.

According to another embodiment the reporter enzyme labeled biomolecule is detectable by a reporter enzyme substrate.

Other Labeling Molecules

According to certain embodiments of the present invention L is an activated hapten such as a hormone, vitamin, peptide, a therapeutic drug, a peptide such as c-myc or FLAG or a drug such as digoxigenin, a chemical moiety such as dinitrophenyl.

Activated Labeling Molecules

The most common active ester of labeling reagents is N-hydroxysulfosuccinimide (NHS). Biotin-NHS and NHS dyes are useful for protein labeling in physiological conditions. Sulfo-N-hydroxy succinimides (S—NHS), including the acid and salt counterparts, described in U.S. Pat. Nos. 5,892,057 and 6,407,263, are water-soluble reagents that have a wide range of applications, including as biotin conjugates. While these activated forms (NSH, S—NSH) are efficient for macromolecules such as proteins and antibodies, they are inefficient for the labeling of small molecules such as peptides, hence creating the need for more efficient activated labels.

The use of activated phenols has been previously explored in organic chemistry. U.S. Pat. No. 5,324,833 teaches the use of pentafluorophenol-activated esters useful for the pre-activation of Fmoc-amino acids for incorporation in solid phase peptide synthesis.

Phenols useful in the preparation of the activated labeling reagent include fluoro-phenol, chloro-phenol, iodo-phenol, thio-phenol, bromo-phenol, hydroxy-phenol, alkoxy-phenol, nitro-phenol sulfo-phenol, naphthalene derivative, their combinations and a salt form of the phenol. In certain embodiments phenol is selected from 2,4,5-trichlorophenol, pentachlorophenol, 2,4,5-triiodophenol, 2,4,5-tribromophenol, pentabromophenol, 2-nitrophenol, 3-nitrophenol, 4-nitrophenol, 2,4,5-trifluorophenol, and 2,4,5,6-tetrafluoro-3-methoxyphenol, tetrafluoro-resorcinol, 3-nitrophenol-5-sulfonic acid, 6-nitro-4-aminophenol-6-sulfonic acid, 8-hydroxy-5,7-dinitro-2-naphthalenesulfonic acid, pentafluorophenol, and 2,4-dinitro-1-naphthol.

Sulfo-phenols are useful in the preparation of an activated labeling reagent, in particular in physiological conditions due to their water solubility, and are encompassed by the present invention.

Biomolecules

A wide variety of biomolecules are suitable for labeling utilizing the activated labeling reagents. In a non-limiting example the following biomolecules maybe labeled by the activated labeling reagent of the present invention: amino acids, peptides and proteins; nucleic acids including nucleotides (deoxyribonucleotides and ribonucleotides), polynucleotides, oligonucleotides, single and double stranded nucleic acids, recombinant, natural and synthetic nucleic acids, DNA, RNA, PNA (peptide nucleic acids), cDNA, lipids, sugars and drugs.

Exemplary Uses

Methods for detecting and isolating targets and substrates, and methods for detecting, diagnosing, staging, monitoring, prognosticating, in vivo imaging, preventing or treating disease, or determining predisposition to disease are just a few example of applications utilizing labeled biomolecules.

Peptide/Protein Examples

Non-limiting examples of applications in which fluorescent labeled biomolecules are used include those described in U.S. Pat. No. 6,818,413, which relates to novel fluorescence-based assays for protein kinases and phosphatases for use in high throughput screening.

Nucleic acid hybridization utilizing labeled nucleic acids, including natural, recombinant or synthetic DNA, cDNA, and RNA, is well known in the art. Multiple diverse methods, techniques and assays are available utilizing labeled nucleic acids.

Another non-limiting use for a labeled biomolecule includes immunoselection techniques. In a non-limiting example, U.S. Pat. No. 5,215,927 teaches an indirect sandwich technique using a biotin-conjugated antispecies immunoglobulin that is directed to one or more non-biotinylated specific antibodies in conjunction with insolubilized avidin. The method is useful for the removal and recovery of specific cell populations from bone marrow, providing excellent recovery of bone marrow and preservation of viable and functional hematopoietic stem cells for transplantation. Mixed populations of T cells or of tumor cells can be conveniently and simultaneously removed with minimal manipulation of the marrow cells.

In one non-limiting example, fluorophore-labeled biomolecules are useful for detecting target molecules. In one non-limiting example, U.S. Pat. No. 5,137,609 teaches an electrophoresis-based assay system for detection of one or more target substances, such as a fluorescent-tagged analyte. The analyte is reacted with an excess amount of fluorescent-tagged binding agent. The reaction mixture is subjected to electrophoresis and the migration of bound and free fluorescent substances are timed at a location where there is a spatial and optical differentiation of the two substances. An optical detector supplies signals corresponding to fluorescent amplitudes of the two substances. Absence of a bound dye signal infers the absence of target analyte in a sample.

Labeling Kits

According to yet another aspect, the present invention provides a kit comprising at least one activated labeling reagent for the labeling of biomolecules, the activated labeling reagent having the formula selected from L-Ph and L-Sp-Ph, wherein L is an activated labeling molecule suitable for labeling of biomolecules, Sp is a spacer molecule that links L to Ph, and Ph is a phenol; and instructions for use.

Labeling reagents useful for inclusion in a kit combination of the present invention include activated forms of biotin, rhodamine and fluorescein According to another aspect the present invention provides a kit comprising at least one labeled biomolecule, the labeled biomolecule prepared according to the method comprising the steps of:
  a) providing an active labeling reagent having the formula selected from L-Ph and L-Sp-Ph, wherein L is an activated labeling molecule suitable for labeling of a biomolecule, Sp is a spacer molecule that links L to Ph, and Ph is a phenol;
  b) providing a biomolecule having at least one functional group selected from the group consisting of an amine moiety, a thio moiety and a hydroxy moiety;
  c) exposing the active labeling reagent to the biomolecule under conditions to allow covalent binding between the reagent and biomolecule to provide a labeled biomolecule; and
  d) precipitating and separating said labeled biomolecule.

Kit Components

The kit includes all reagents and methods useful for the labeling of biomolecule by said labeling reagent including:
  a) Activated labeling reagent having the formula selected from L-Ph and L-Sp-Ph, wherein L is an activated labeling molecule suitable for labeling of a biomolecule, Sp is a spacer molecule that links L to Ph, and Ph is a phenol. In certain embodiments L is selected from the group consisting of biotin, rhodamine and fluorescein.
  b) Reaction solution having a composition suitable for the dissolving the active labeling reagent and the biomolecule, and promoting the labeling reaction. The reaction solution is composed of a buffer or organic solvent or combination therefore; wherein the reaction solution is a phosphate buffer, bicarbonate buffer, borate buffer, dimethylformamide, dimethylacetamide, dimethylsulfoxide, N-methylpyrolidon and their combinations. The reaction solution may further include additives such as diisopropylethylamine or triethylamine.
  c) Stop solution having properties that can stop the reaction by disarming the active labeling reagents or activating with it. The stop reagent is preferably a primary amine including ethanolamine or glycine.
  d) Precipitation solution having ability to separate the labeled biomolecule from the free label by precipitating the labeled biomolecule. In one embodiment the precipitation solution is selected from diethyl ether, t-butyl-methyl ether, dioxane, ethyl acetate and dichloromethane.
  e) Separation solution having a composition suitable for the dissolving the labeled biomolecule, and useful for separating on a column. The separation solution is composed of a buffer or organic solvent or combination thereof; wherein the reaction solution is a phosphate buffer, bicarbonate buffer, borate buffer Tris buffer, acetonitryl, methanol and their combinations.
  f) Separation gel having ability to separate the labeled biomolecule from the free label and by column separation. The separation gel is composed from a matrix suitable for biomolecule separation; wherein the gel is an ion exchange column, size exclusion column, affinity chromatography, or reverse phase column.

The invention will better be understood by reference to the following examples. The skilled artisan will appreciate that the following examples are merely illustrative and serve as non limitative exemplification of the principles of the present invention and that many variations and modifications are possible within the scope of the currently claimed invention as defined by the claims which follow.

EXAMPLES

The following abbreviations are used herein:
DIEA Diisopropyl-ethylamine
DMF Dimethylformamide
HOBT 1-Hydroxybenzotriazole hydrate
PFP Pentafluorophenol
DCC N,N'-Dicyclohexylcarbodiimide
DCM Dichloromethane
Ahx aminohexanoic acid
TFA Trifluoroacetic acid
DMAP dimethylaminopyridine
DIC N,N'-Diisopropylcarbodiimide
TBTU O-(1H-benzotriazole-1-yl)-N,N,N',N'-tetramethyluronium tetrafluoroborate
MW molecular weight
O.D. optical density Example 1

Synthesis of a Biotin Pentafluorophenyl Active Ester

A biotin pentafluorophenyl active ester, referred to herein as d-biotin-O-PFP, was synthesized as follows: 1 mmol of d-biotin, 0.1 mmol of DIEA, 0.1 mmol HOBT, 1.2 mmol PFP were dissolved in 10 ml DMF. 1.1 mmol of DCC was added to the mixture. The reaction was carried out for 24 hours at room temperature while shaking. The white crystals, which appeared in the mixture, were filtered out. 10 ml DCM was added to the solution to precipitate d-biotin-O-PFP. The precipitate was washed with DCM and crystallized from a methanol: ethyl acetate solution. The yield of d-biotin-O-PFP was 53%, Melting point 172-174° C., MW of 410 gr/mol, O.D. of 271 nm. The structure of d-biotin-O-PFP is shown in FIG. 1A.

Example 2

Synthesis of Pentafluorophenyl Active Ester of D-Biotin Having a β-Alanine Spacer A pentafluorophenol active ester of biotin having a β-alanine spacer, referred to herein as d-biotin-βAla-O-PFP, was synthesized according to the following method: 2 mmol βAla-O-tBu was dissolved in 10 ml DMF and 0.2 mmol DIEA. Two (2) mmol d-biotin-O-PFP was added to the reaction. The reaction was carried out for 20 hours at room temperature. d-biotin-βAla-O-tBu was precipitated and washed with DCM. Cleavage of the protecting group (tBu) was carried out in 1 ml TFA+5% water for 3 hours. The acid was evaporated in a vacuum over a KOH pellet. d-biotin-βAla was washed several times with diethyl ether and dried.

1 mmol of d-biotin-βAla, 0.1 mmol of DIEA, 0.1 mmol HOBT, 1.2 mmol PFP were dissolved in 10 ml DMF. 1.1 mmol of DCC was added to the mixture. The reaction was carried out for 24 hours at room temperature while shaking.

Figure 1B:
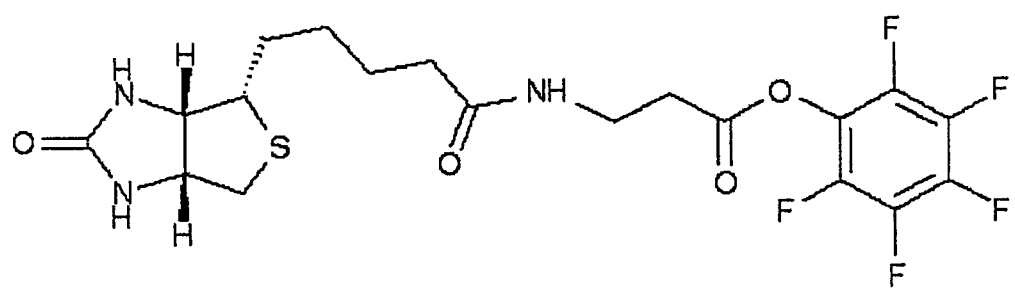

The white crystals, which appeared in the mixture were filtered out. 10 ml DCM was added to the solution to precipitate d-biotin-βAla-O-PFP. The precipitate was washed with DCM and crystallized from a methanol: ethyl acetate solution. The structure of d-biotin-βAla-O—PFP is shown in FIG. 1B.

Example 3

Synthesis of Pentafluorophenol Active Ester of d-Biotin with Aminohexanoic (Aminocaproic) Acid Spacer A pentafluorophenol active ester of d-biotin having a aminohexanoic acid spacer, referred to herein as d-biotin-Ahx-O-PFP, was synthesized according to the following method: 2 mmol Ahx-O-tBu was dissolved in 10 ml DMF and 0.2 mmol DIEA. 2 mmol d-biotin-O-PFP was added to the reaction. The reaction was carried out for 20 hours at room temperature. d-biotin-Ahx-O-tBu was precipitated and washed with DCM. Cleavage of the protecting group (tBu) was carried out in 1 ml TFA+5% water for 3 hours. The acid was evaporated in vacuum over KOH pellet. d-biotin-Ahx was washed several times with diethyl ether and dried.

Figure 1C:
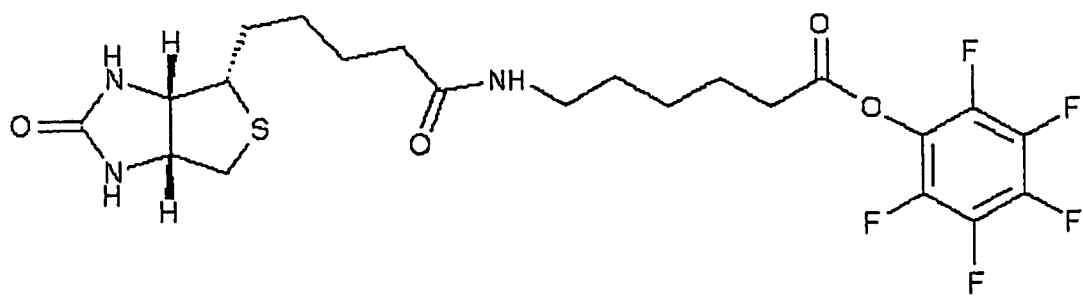

1 mmol of d-biotin-Ahx, 0.1 mmol of DIEA, 0.1 mmol HOBT, 1.2 mmol PFP were dissolved in 10 ml DMF. 1.1 mmol of DCC was added to the mixture. The reaction was carried out for 24 hours at room temperature while shaking. White crystals that appeared in the mixture were filtered out. 10 ml DCM was added to the solution to precipitate d-biotin-Ahx-O-PFP. The precipitate was washed with DCM and crystallized from methanol: ethyl acetate solution. The structure of d-biotin-Ahx-O-PFP is shown in FIG. 1C.

Example 4

Synthesis of Pentafluorophenol Active Ester of Biotin Having a di-Peptide Spacer A pentafluorophenol active ester of d-biotin having a di-aminohexanoic acid spacer referred to herein as d-biotin-Ahx-Ahx-O-PFP, was synthesized according to the following method: about 1 g Wang resin (100-200 mesh, polypropylene 1% DVB), was swollen in DMF for 1 hour. The resin was washed several times with DMF.

Fmoc-Ahx-OH (1.6 mmol) was dissolved in 10 ml DCM and added to the resin, and 2.4 mmol of pyridine, and 1.6 mmol 2,6-dichlorobenzoyl chloride were added to the reaction. The reaction was carried out for 20 hours at room temperature. The resin was washed several times with DCM, DCE. The remaining hydroxyl groups were blocked with 0.3 ml benzoyl chloride and 0.3 ml pyridine in 8 ml DCE for 2 hours. The resin was washed with DCE, DCM. The Fmoc protecting group was removed by incubating the resin in 20% piperidine in DMF 3 times for 10 minutes each time. The resin was washed several times with DMF, DCM. 2.4 mmol of the second Fmoc-Ahx-OH was coupled to the resin with 2.4 mmol DIC and 2.4 mmol HOBt dissolved in DMF for 2 hours. 2.4 mmol of d-biotin, 2.4 mmol TBTU, 4.8 mmol DIEA, and 2.4 mmol HOBt were dissolved in DMF and added to the resin. The reaction was carried out for 2 hours at room temperature. The resin was washed several times with DMF, DCM, DMF. The resin was dried in vacuum. The product was cleaved from the resin by 1 ml of 95% of TFA+5% water for 2 hours. The acid was evaporated in vacuum over KOH pellet. d-biotin-Ahx-Ahx was washed several times with diethyl ether and dried.

Figure 2A:
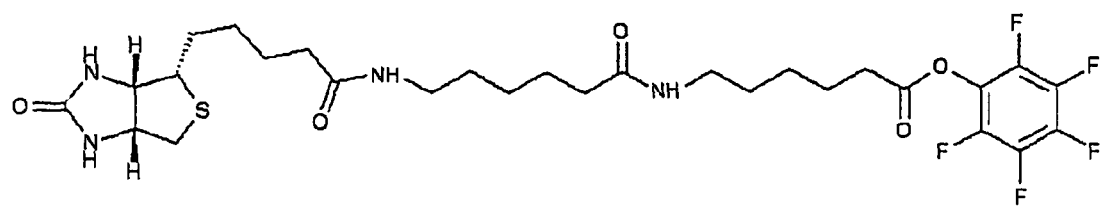
FIGS. 2A-2B show molecular structures of certain activated labeling reagents of the invention.

1 mmol of d-biotin-Ahx-Ahx, 0.1 mmol of DIEA, 0.1 mmol HOBT, 1.2 mmol PFP were dissolved in 10 ml DMF. 1.1 mmol of DCC was added to the mixture. The reaction was carried out for 24 hours at room temperature while shaking. The white crystals, which appeared in the mixture were filtered out. 10 ml DCM was added to the solution to precipitate d-biotin-Ahx-O-PFP. The precipitate was washed with DCM and crystallized from a methanol: ethyl acetate solution. The structure of d-biotin-Ahx-Ahx-O-PFP is shown in FIG. 2A.

Example 5

Synthesis of a Pentafluorophenol Active Ester of Biotin with a Cleavable Spacer

A pentafluorophenol active ester of biotin having a 2-aminoethyl-carboxymethyl disulfide cleavable spacer linkage between Cysteaminium and Thioglutaric acid), herein referred to as d-biotin-2-aminoethyl-carboxymethyldisulfide-O-PFP was synthesized in the following manner: 2 mmol $H_2N—(CH_2)_2—S—S—(CH_2)_2—COOH$ was dissolved in 10 ml DMF and 0.2 mmol DIEA. 2 mmol d-biotin-O-PFP was added to the reaction. The reaction was carried out for 20 hours at room temperature. d-biotin-HN—(CH2)2-S—S—(CH2)2-COOH was precipitated and washed with DCM, diethyl ether and dried.

Figure 2B:
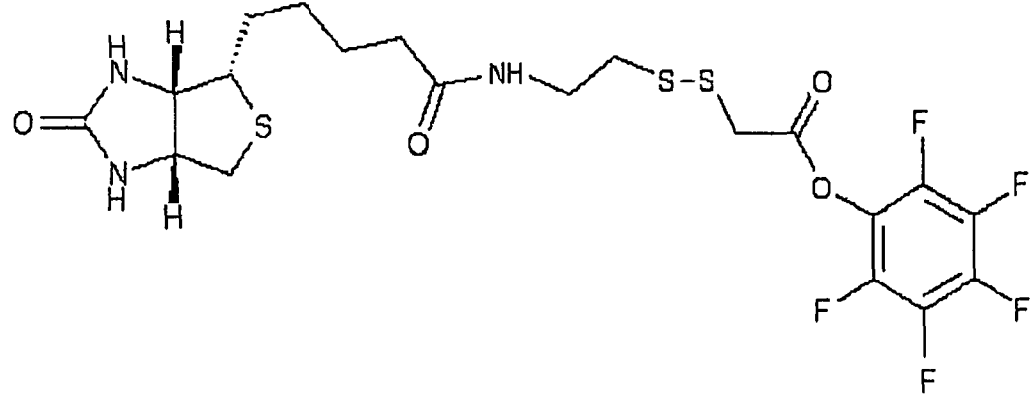

1 mmol of d-biotin-HN—(CH2)2-S—S—(CH2)2-COOH, 0.1 mmol of DIEA, 0.1 mmol HOBT, 1.2 mmol PFP were dissolved in 10 ml DMF. 1.1 mmol of DIC was added to the mixture. The reaction was carried out for 24 hours at room temperature while shaking. 10 ml DCM was added to the solution to precipitate d-biotin-HN—$(CH_2)_2$—S—S—$(CH_2)_2$—COO-PFP. The precipitate was washed with DCM and crystallized from a methanol:ethyl acetate solution. The structure of d-biotin-2-aminoethyl-carboxymethyldisulfide-O-PFP is shown in FIG. 2B.

Example 6

Synthesis of Dinitrophenyl-d-Biotin

A dinitrophenyl derivative of biotin was prepared in the following manner: 1 mmol of d-biotin, 0.1 mmol of DIEA, 0.1 mmol HOBT, 1.2 mmol 3,5-dinitrophenol were dissolved in 10 ml DMF. 1.1 mmol of DCC was added to the mixture. The reaction was carried out for 24 hours at room temperature while shaking. The white crystals, which appeared in the mixture, were filtered out. 10 ml DCM was added to the solution to precipitate 3,5-dinitrophenyl-d-biotin. The precipitate was washed with DCM and crystallized from a methanol:ethyl acetate solution.

Example 7

Synthesis of a Fluorescein Pentafluorophenyl Active Ester

Figure 3A:
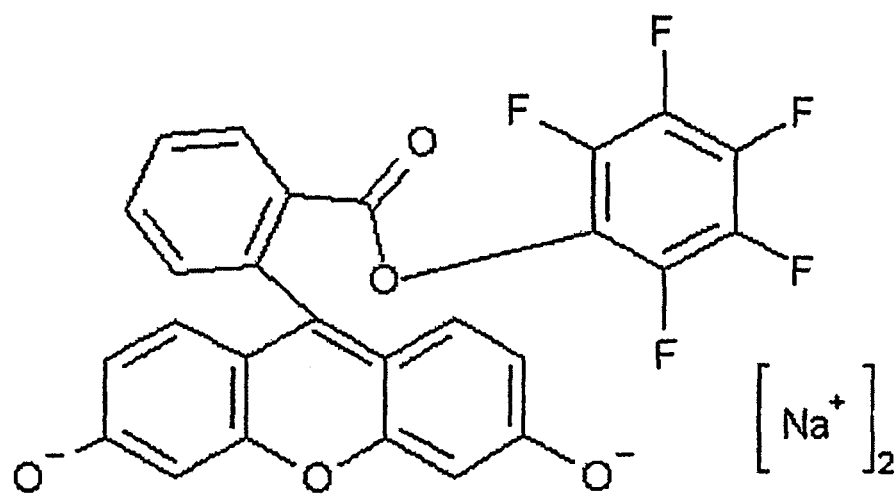
FIGS. 3A-3B show molecular structures of certain activated labeling reagents of the invention.

A Fluorescein pentafluorophenyl active ester, Fluorescein-O-PFP, was prepared in the following manner: 1 mmol of Fluorescein, 0.1 mmol of DMAP, 0.1 mmol HOBT, 1.2 mmol PFP were dissolved in 10 ml Dioxane/DMF solution. 1.1 mmol of DIC was added to the mixture. The reaction was carried out for 24 hours at room temperature while shaking. The solution was evaporated and 10 ml of hexane was added to the solution to precipitate Fluorescein-O-PFP. The precipitate was washed with hexane and crystallized from a hexane: dioxane solution to give orange powder. Product yield was 95%, MW of 488 gr/mol, O.D. of 270,496 nm. The structure of Fluorescein-O-PFP is shown in FIG. 3A.

Example 8

Synthesis of Rhodamine Pentafluorophenyl Active Ester

Figure 3B:
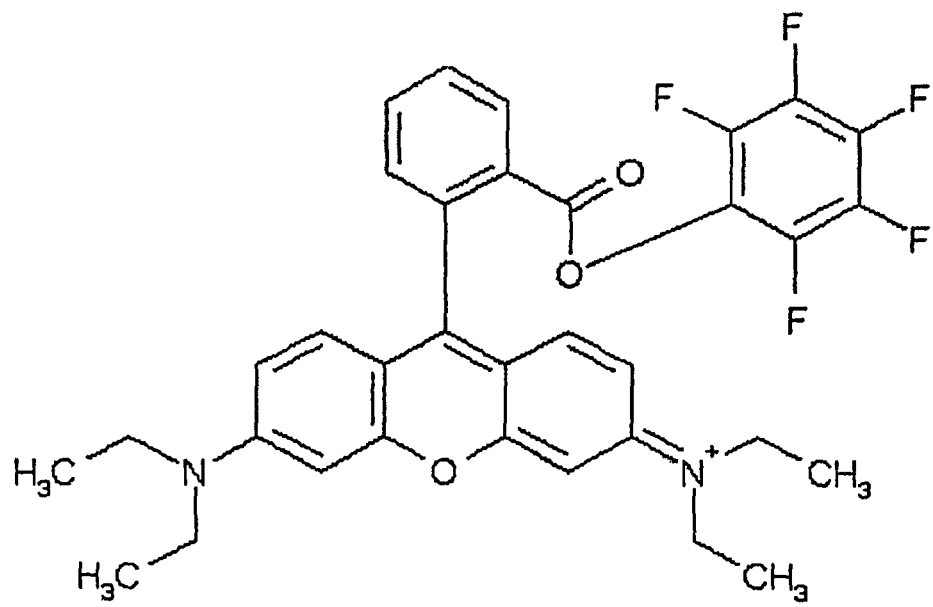

A rhodamine pentafluorophenyl active ester, Rhodamine-O-PFP, was prepared by dissolving 1 mmol of Rhodamine, 0.1 mmol of DIEA, 0.1 mmol HOBT, 1.2 mmol PFP in 10 ml DMA. 1.1 mmol of DIC was added to the mixture. The reaction was carried out for 24 hours at room temperature while shaking. The white crystals that appeared in the mixture were filtered out. 10 ml DCM was added to the solution to precipitate rhodamine-O-PFP. The precipitate was washed with DCM and crystallized as HCl-salt. Product yield was 93%, MW of 645 gr/mol, O.D. of 270, 543 nm. The structure of Fluorescein-O-PFP is shown in FIG. 3B. Rhodamine-O-PFP was dissolved in methanol and analyzed by Reverse phase HPLC on C-18 column with acetonitril/water gradient. FIG. 8A shows comparable analysis by HPLC of rhodamine-O-PFP (a), and rhodamine (b).

Example 9

Coupling of d-Biotin-O-PFP to a Lysine Side Chain

Figure 4:
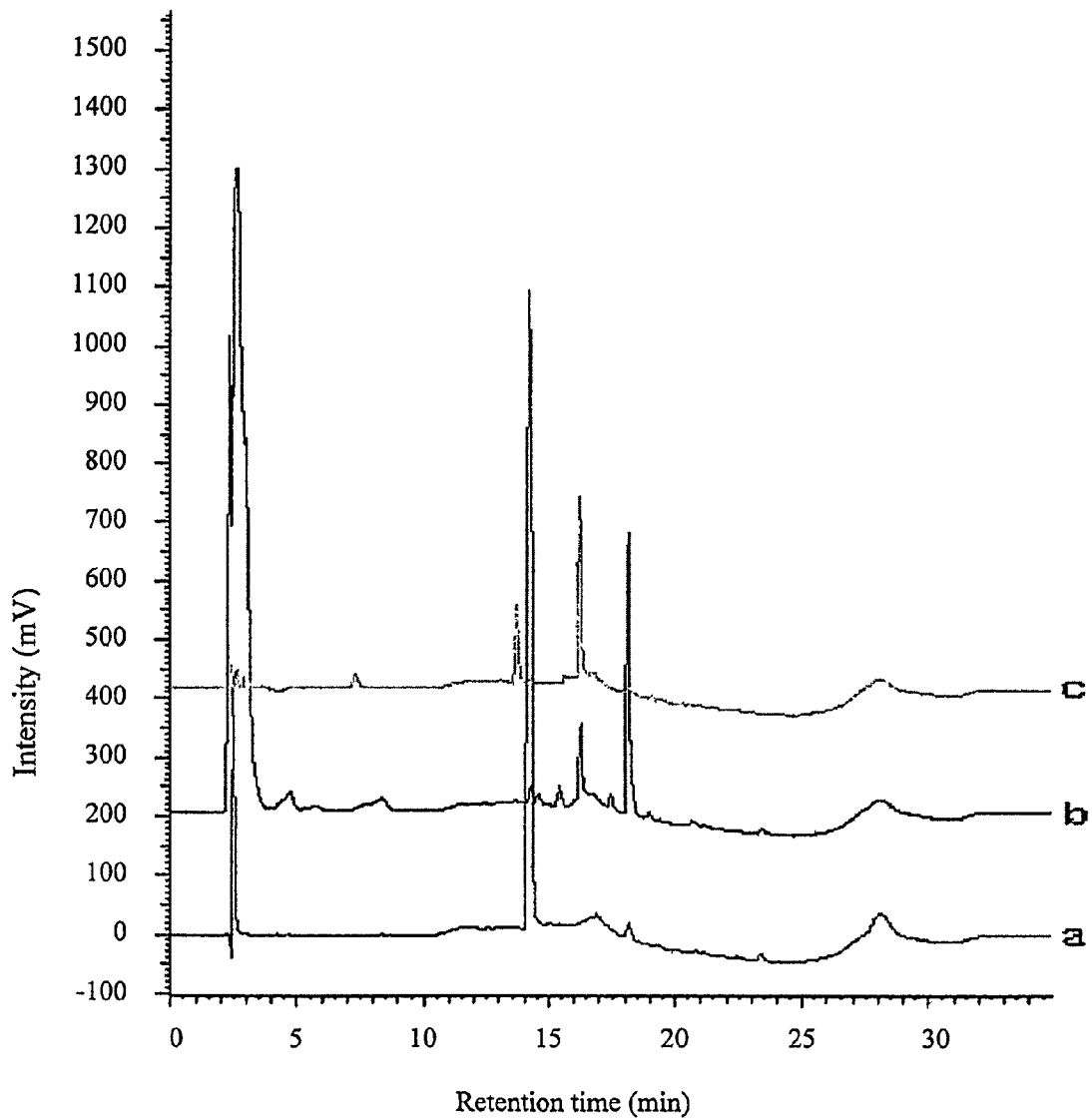
FIG. 4 shows HPLC analysis of Fmoc-Lys-OH (a) and d-biotin-O-PFP (c) compared to Fmoc-Lys (biotin)-OH (b).

Coupling of d-biotin-O-PFP (from example 1) to a lysine side chain of an amino acid was accomplished as follows: 1.6 mg of Fmoc-Lys-OH was dissolved in 0.32 ml NMP with 1% DIEA by heating to 70° C., the mixture was cooled to room temperature and 1.6 mg of d-biotin-O-PFP was added, the reaction was mixed and incubated for 20 hours at room temperature. The product Fmoc-Lys(d-biotin)-OH was precipitated with 1 ml ice-cold t-butyl-methyl ether and incubated for 15 minutes at −20° C. the precipitate was collected by centrifugation for 1 minute at micro-centrifuge. The pellet was washed two times with 1 ml ice-cold t-butyl-methyl ether, and dried on air. Fmoc-Lys (d-biotin)-OH was dissolved in water and analyzed by Reverse phase HPLC on C-18 column with acetonitril/water gradient. FIG. 4 shows comparable analysis by HPLC of Fmoc-Lys-OH (a), d-biotin-O-PFP (c), and Fmoc-Lys (d-biotin)-OH (b).

Example 10

Figure 5A:
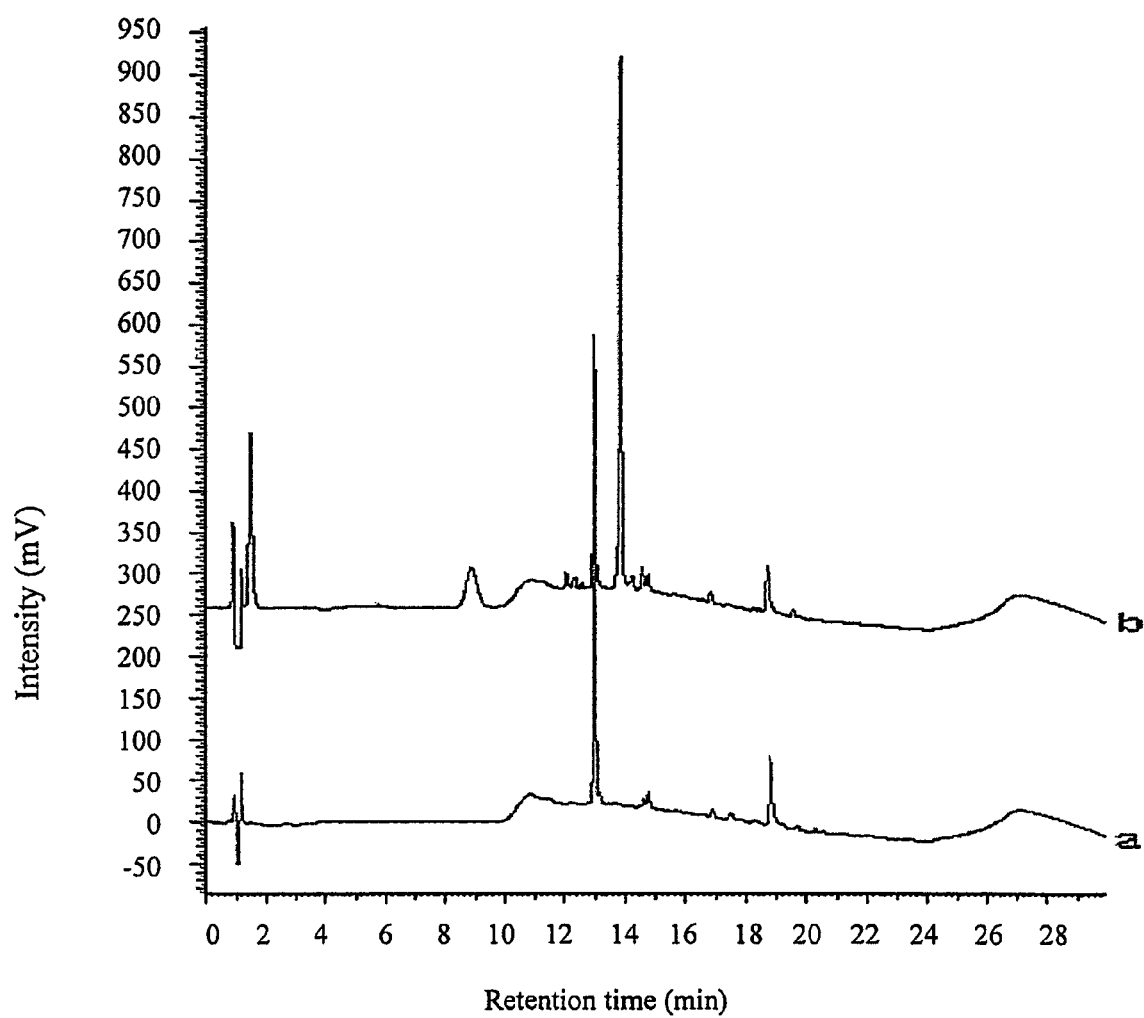
FIG. 5A shows HPLC analysis of a free hexapeptide (a) compared to a d-biotin labeled peptide (b) of the present invention.

Coupling of d-Biotin-O-PFP to Amino Terminus of a Peptide d-biotin-O-PFP was conjugated to the N-terminus of a model peptide, TRAP-6 (Thrombin Receptor Activating Peptide-6) in the following manner: The TRAP-6 hexapeptide was synthesized as previously described (Kaufmann R. et al., J. Neurooncol. 42, 131, 1999). 10 mg of TRAP-6 hexapeptide were dissolved in 0.5 ml DMF, 10.6 mg (2 eq) of d-biotin-O-PFP were dissolved in 0.5 ml DMF with 1% DIEA and added to the hexapeptide, and the reaction was mixed and incubated for 3 hours at room temperature. The product, d-biotin-hexapeptide was precipitated with 10 ml ice-cold ether, and collected by centrifugation for 2 minutes at micro-centrifuge. The pellet was washed two times with 5 ml ice-cold ether, and dried on air. The d-biotin-hexapeptide was dissolved in water and analyzed by Reverse Phase HPLC on C-18 column with acetonitril/water gradient. FIG. 5A shows comparable HPLC analysis of the free hexapeptide (a), and d-biotin-hexapeptide (b).

Example 11

Figure 5B:
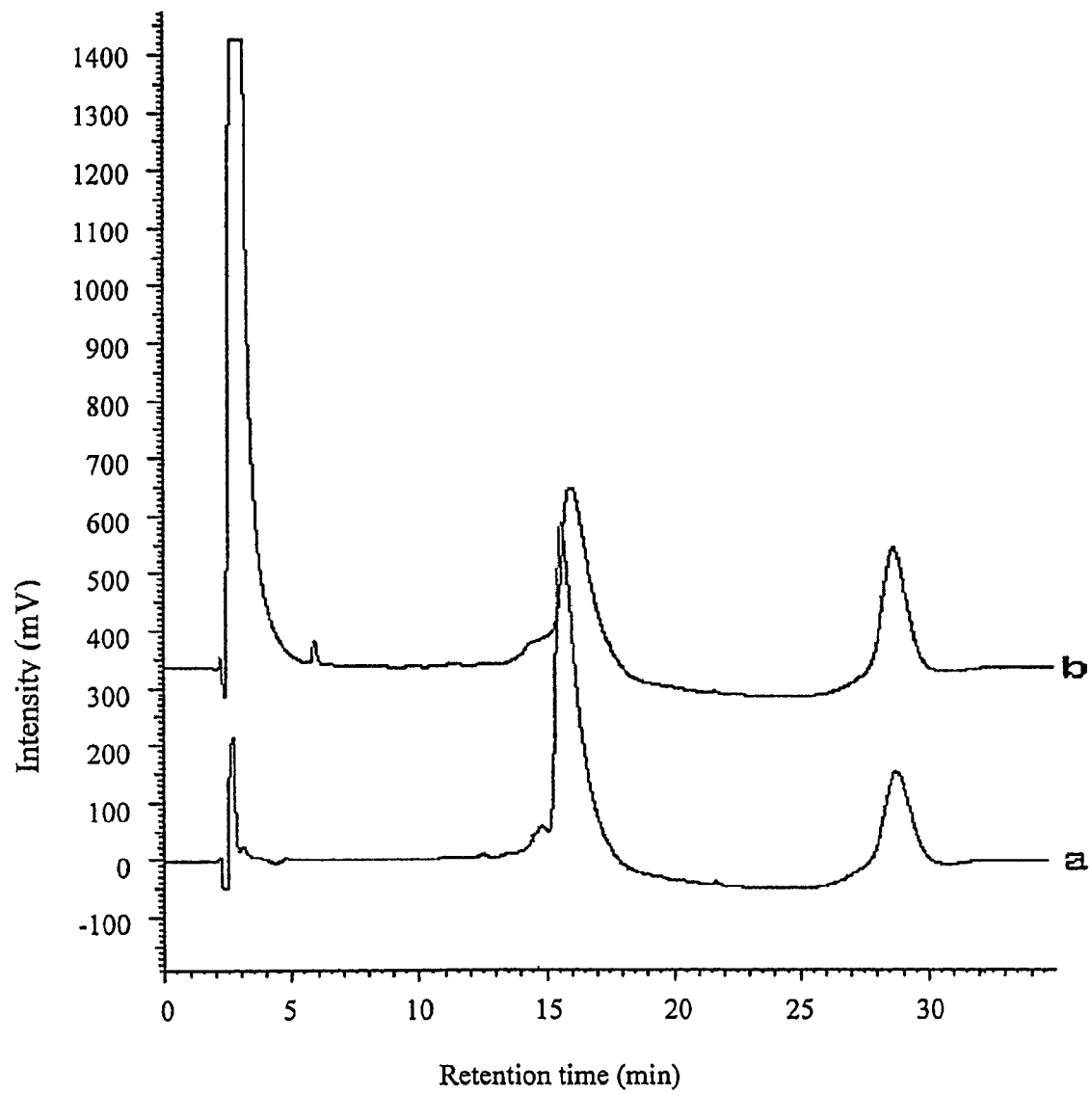
FIG. 5B shows HPLC analysis of a free protein (BSA) (a) compared to a d-biotin labeled protein (b) of the present invention.

Coupling of d-Biotin-O-PFP to a Protein d-biotin-O-PFP was conjugated to a model protein, BSA (Bovine Serum Albumin) in the following manner: 1.3 mg of BSA (Bovine Serum Albumin—fraction V) was dissolved in 0.13 ml water, 0.7 mg of d-biotin-O-PFP was dissolved in 0.07 ml DMF with 1% DIEA and added to the BSA, the reaction was mixed and incubated for 20 hours at room temperature. The reaction mixture was further diluted in 20 mM sodium bicarbonate solution and d-biotin-BSA was separated on G50 agarose size exclusion gel. The d-biotin-BSA was analyzed by Reverse phase HPLC on C-18 column with acetonitril/water gradient (FIG. 5B, and peptide mapping as previously described (Bradburne J A, Appl. Environ. Microbiol. 59:663, 1993). FIG. 5B shows comparable analysis of free BSA (a), and d-biotin-BSA (b) as determined by HPLC.

Example 12

Biotin Labeling Kit: Components and Instructions for Use

Kit Components
- Biotin-OPFP reagent—about 5 mg
- Reaction Solution (1% DIEA in DMA)—about 2 ml
- Stop Solution (1 M ethanolamine in DMA)—about 50 μl
- Precipitation Solution (t-butyl-methyl ether)—about 15 ml
- Separation Gel (G10 agarose)—about 2 ml
- Separation Solution (20 mM sodium bicarbonate buffer)—about 4 ml
- Spin Columns—5 columns
- Micro-centrifuge polypropylene tubes—5 tubes A. Biotinylation
1. Weigh 0.5-1 mg of the Biotin-OPFP reagent in a polypropylene tube, and dissolve in 50 μl-100 μl reaction solution (final concentration of 1 mg/ml).
2. Weigh 1-2 mg of your biomolecule in 2 ml polypropylene tube, and dissolve in minimal amount of (5-10 μl) DMSO (dimethylsulfoxide) or reaction solution. Add 50 μl reaction solution.
3. Calculate the amount of Biotin solution that should be added to the biomolecule according to the formula (molar ratio from 2 to 6 can be applied)

$$X = \frac{\text{molar ratio} \times \text{Biomolecule mg} \times 400 \times \text{Biotin solution volume}}{\text{Biotin mg} \times \text{Biomolecule MW}}$$

4. Add X μl of Biotin solution to the peptide solution. Mix by vortex.
5. Incubate for 2-3 hours at room temperature.
6. Add 5 μl stop solution. Mix by vortex.

B. Purification

Part 1: Precipitation
1. Add 1 ml of ice cold Precipitation Solution to the reaction mix, vortex. The precipitate that appears, contain the labeled Biomolecule.
2. Cool the tube on ice for 15-20 minutes, for improved precipitation of the product.
3. Centrifuge the tube for 1 minute at 3000 G, pellet appears in the bottom of the tube. Carefully remove the solution; the pellet contains the biotinylated Biomolecule.

4. Add 0.2 ml ice cold Precipitation Solution to the pellet, and suspend by vortex.
5. Centrifuge the tube for additional 1 minute at 3000 g, and carefully remove the solution, try to remove all solution residuals, dry* the pellet on air.

Part 2: Column Separation
1. Dissolve the peptide in 0.1-0.2 ml of Separation Solution.
2. Resuspend the Separation Gel before use.
3. Transfer 0.2-0.4 ml of suspended Gel into the column. Place the column into a collection tube and centrifuge for 1 minute at 500 G to remove the solution.
4. Remove the spin column from the collection tube and discard the flow-through solution.
5. Wash the column once with 0.2 ml Separation Solution (add solution to the column, centrifuge, and discard the flow-through solution.
6. Add the dissolved Biomolecule to the top of the gel in the spin column. Centrifuge the tube for 1 minute at 500×g. The flow-through contains your labeled Biomolecule.
7. Store aliquots of your Biomolecule at −20° C. to −70° C.

Example 13

Kit for Labeling with Fluorescein

Kit Components
Fluorescein-OPFP reagent—about 5 mg
Reaction Solution (1% TEA in DMF)— about 2 ml
Stop Solution (1 M ethanolamine in DMA)—about 50 µl
Precipitation Solution (di-ethyl ether)—about 15 ml
Separation Gel (G25 agarose)—about 2 ml
Separation Solution (20 mM phosphate buffer saline)—about 4 ml
Spin Columns—5 columns
Micro-centrifuge polypropylene tubes—5 tubes
Kit labeling procedures are as described in example 12.

Example 14

Kit for Labeling with Rhodamine

Kit Components
Fluorescein-OPFP reagent—about 5 mg
Reaction Solution (1% TEA in NMP)—about 2 ml
Stop Solution (1 M ethanolamine in DMA)—about 50 µl
Precipitation Solution (di-ethyl ether)—about 15 ml
Separation Gel (G25 agarose)—about 2 ml
Separation Solution (20 mM phosphate buffer saline)—about 4 ml
Spin Columns-5 columns
Micro-centrifuge polypropylene tubes—5 tubes
Kit labeling procedures are as described in example 12.
Example 15 Synthesis of Biotin with Fatty Acid (11-aminoundecanoic Acid) Spacer Pentafluorophenyl Active Ester The biotinylated lipid reagent, d-biotin-11-aminoundecanoyl-O-PFP, was prepared according to the following method: 2 mmol 11-aminoundecanoic acid was dissolved in 10 ml n-Hexane and 0.2 mmol DMAP. 2 mmol d-biotin-O-PFP was added to the reaction. The reaction was carried out for 20 hours at room temperature. The hexane was evaporated and the d-biotin-11-aminoundecanoic acid was washed with diethyl ether and dried.

Figure 6A:
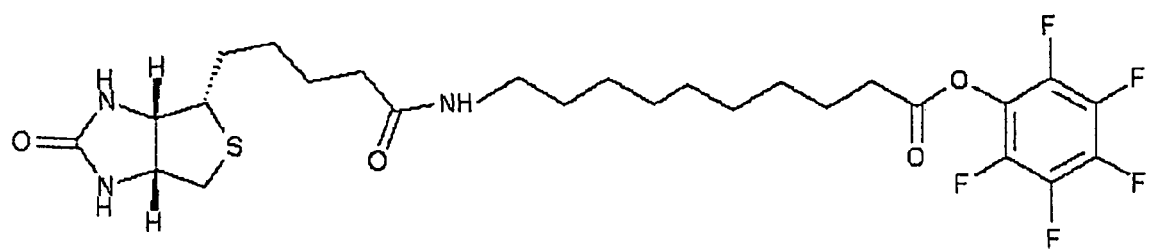
FIG. 6A shows the structure of the activated labeling reagent d-biotin-11-aminodecanoyl-O-PFP.

The following were added to the mixture: 1 mmol of d-biotin-11-aminoundecanoic acid, 0.1 mmol of DIEA, 0.1 mmol HOBT, 1.2 mmol PFP were dissolved in 10 ml Hexane/DCM. 1.1 mmol of DIC was added to the mixture. The reaction was carried out for 24 hours at room temperature while shaking. The hexane/DCM was evaporated and d-biotin-11-aminoundecanoyl-O-PFP acid was washed with diethyl ether and dried. d-biotin-11-aminoundecanoyl-O-PFP was crystallized from methanol:ethyl acetate solution. FIG. 6A shows the chemical structure of d-biotin-11-aminoundecanoyl-O-PFP.

Example 16

Coupling of Biotin to a Nucleotide (Cytosine)

Figure 6B:
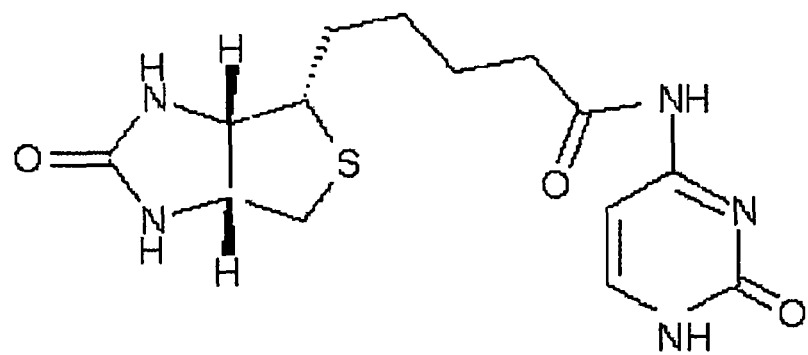
FIG. 6B shows the structure of a labeled nucleotide: d-biotin-cytosine-O-PFP.

A biotinylated nucleotide, d-biotin-cytosine, was synthesized for use in nucleic acid labeling applications. Two (2) mmol d-biotin-O-PFP (example 1) was dissolved in 10 ml DMF and 0.2 mmol DIEA. Two (2) mmol of dry cytosine was added to the reaction. The reaction was carried out for 18 hours at room temperature. d-biotin-cytosine was precipitated and washed with DCM. Purified d-biotin-cytosine was crystallized from methanol. FIG. 6B shows the chemical structure of d-biotin-cytosine.

Example 17

Figure 7A:
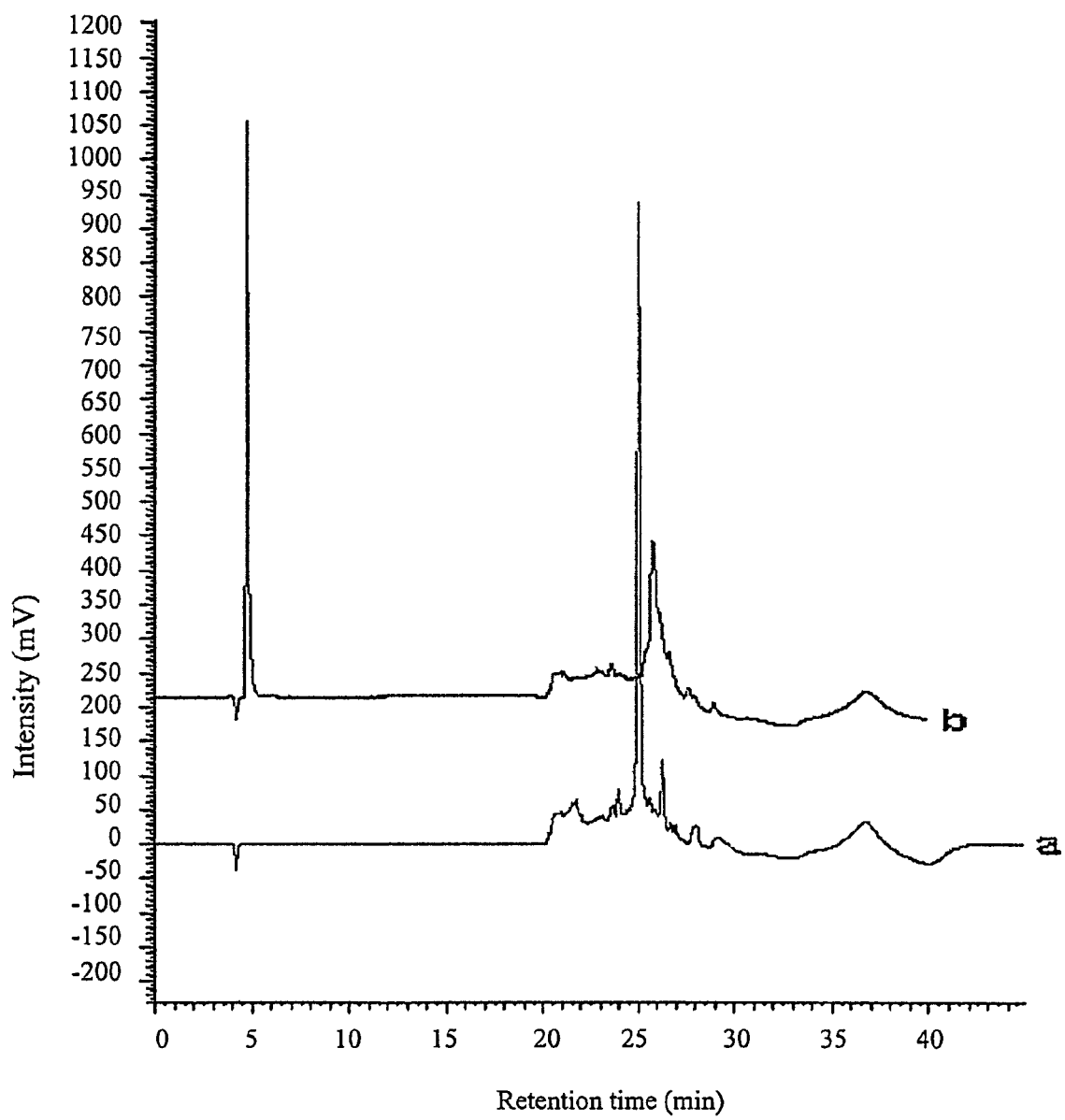
FIG. 7A shows HPLC analysis of free MOG peptide (a) compared to a d-biotin labeled MOG peptide (b) of the present invention.

Coupling of d-Biotin-O-PFP to a 21 Amino Acid Peptide d-biotin-O-PFP was conjugated to a 21 amino acid model peptide, MOG peptide 35-55 (Myelin Oligodendrocyte Glyco-protein peptide fragment 35-55 Rat, Mouse) in the following manner: The MOG peptide 35-55 (MEVGWYR PPFSRVVHLYRNGK (SEQ ID NO: 1)) was synthesized as previously described (Liu, J., 1998, Nat. Med. 4, 78). 10 mg of MOG peptide were dissolved in 0.5 ml DMA, 10 mg of d-biotin-O-PFP were dissolved in 0.5 ml DMA with 0.1 M Triethylamine and added to the peptide, the reaction was mixed and incubated for 3 hours at room temperature. The product d-biotin-MOG was precipitated with 10 ml ice-cold ether, and collected by centrifugation for 2 minutes at microcentrifuge. The pellet was washed twice with 5 ml ice-cold ether, and air dried. d-biotin-MOG was dissolved in water and analyzed by reverse phase HPLC on C-18 column with an acetonitril/water gradient. FIG. 7A shows the comparable analysis by HPLC of free MOG peptide (a), and d-biotin-MOG peptide (b).

Example 18

Figure 7B:
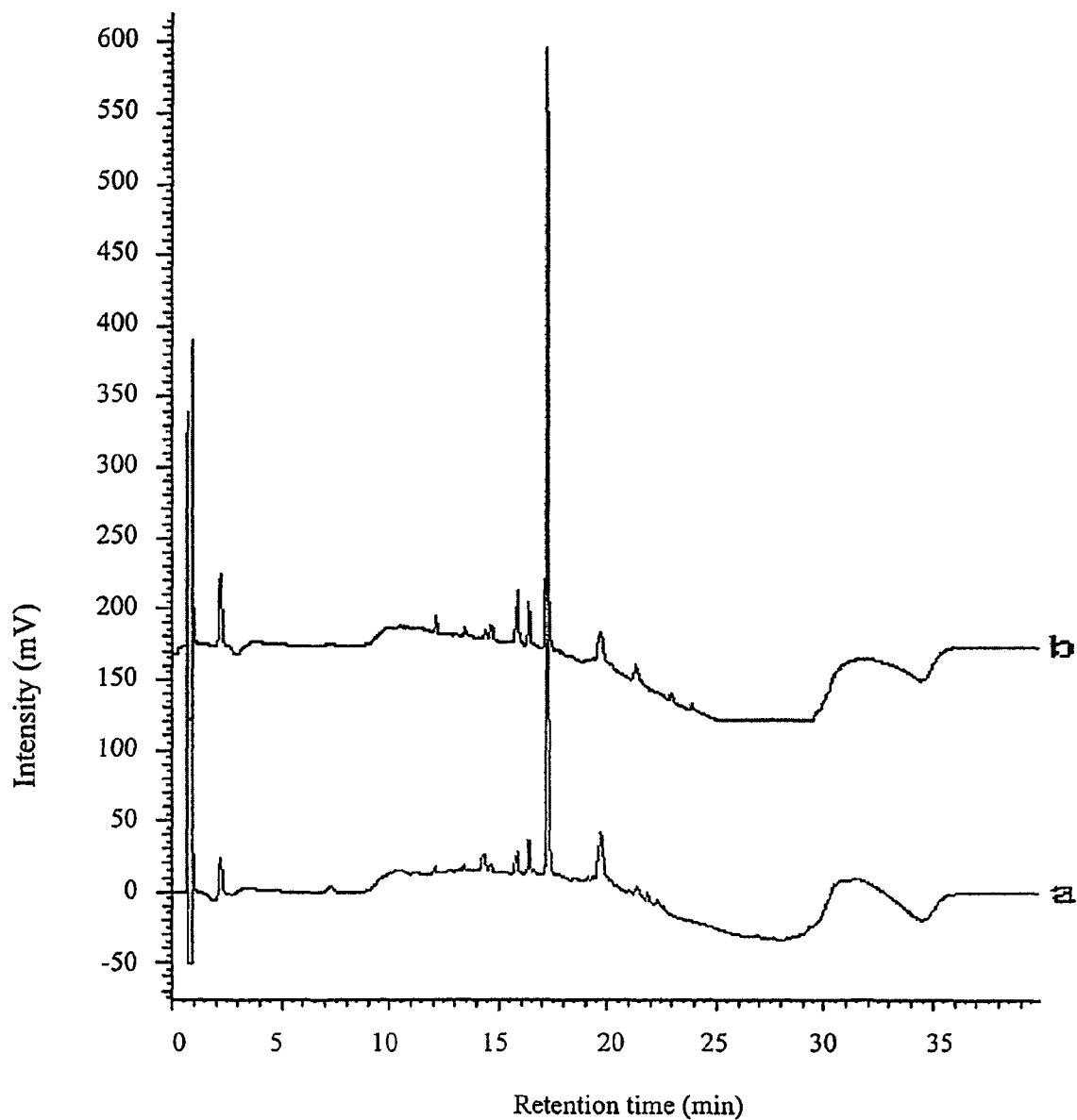
FIG. 7B shows HPLC analysis of a freshly prepared d-biotin-O-PFP (a) compared to d-biotin-O-PFP following four months storage at room temperature.

Stability Test of d-Biotin-O-PFP d-biotin-O-PFP was synthesized as previously described in Example 1 and analyzed by HPLC. The product was shelved for 4-6 months. After that time the shelved product was analyzed by HPLC. d-biotin-O-PFP was dissolved in methanol and analyzed by reverse phase HPLC on C-18 column with acetonitril/water gradient. FIG. 7B shows comparable analysis by HPLC of d-biotin-O-PFP freshly prepared (a), and d-biotin-O—PFP following 4 months storage at room temperature (b).

Example 19

Labeling of a Peptide with Biotin Labeling Kit

The TRAP-6 hexapeptide was synthesized as previously described (Kaufmann R. et al., 1999, J. Neurooncol. 42, 131-

136). Two (2) mg of the peptide were labeled and purified with the use of biotin labeling kit as described in example 12.

Example 20

Labeling of a Peptide with Rhodamine Labeling Kit

Figure 8B:
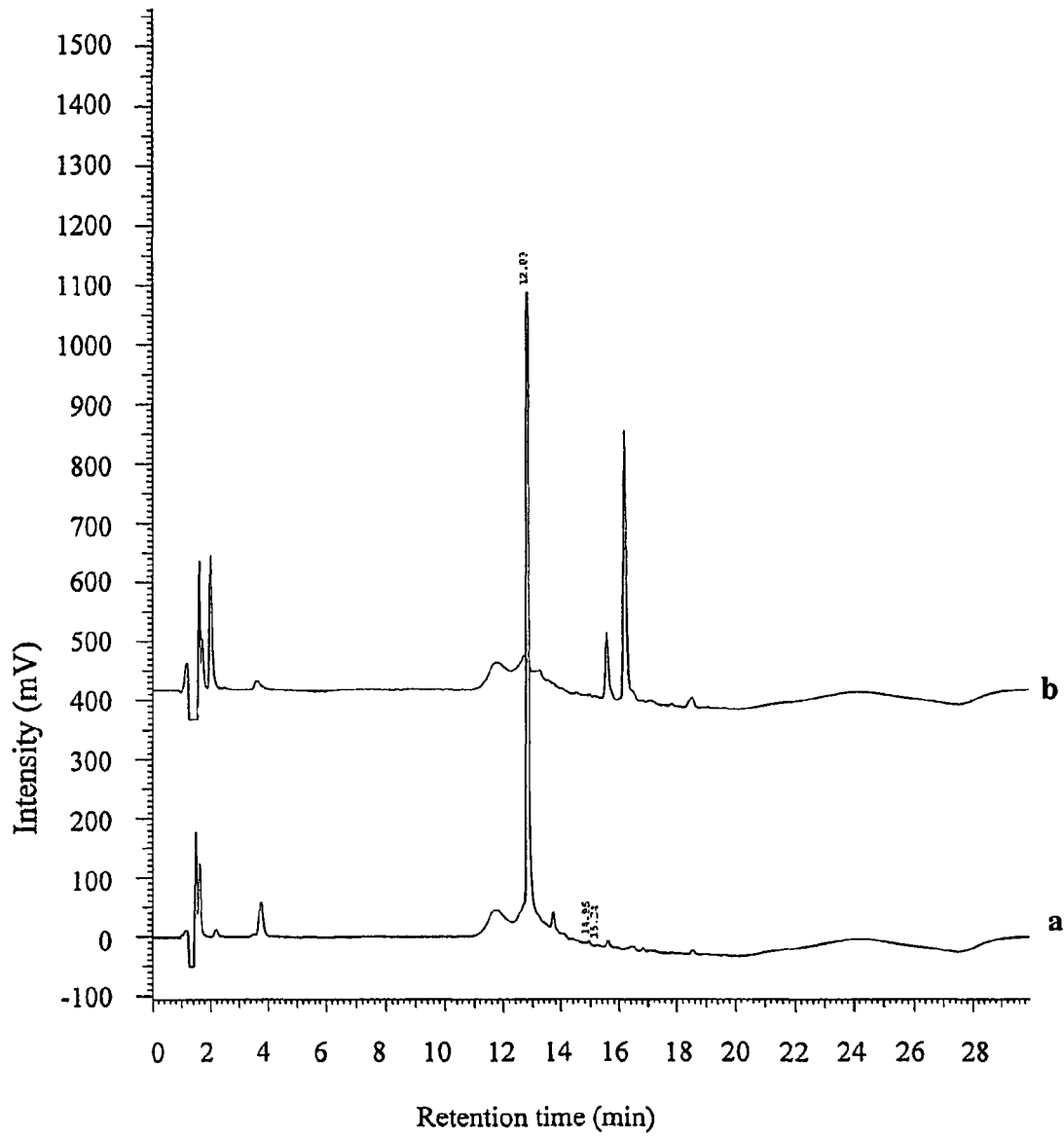
FIG. 8B shows HPLC analysis of free hexapeptide (a) compared to a rhodamine labeled hexapeptide (b).

The TRAP-6 hexapeptide was synthesized as previously described (Kaufmann R. ibid). Two (2) mg of the peptide were labeled and purified with the use of Rhodamine labeling kit as described in example 13. Labeled peptide gave deep red powder. FIG. 8B shows the comparable analysis by HPLC of the free peptide (a), and the rhodamine labeled peptide (b).

Example 21

Labeling of a Peptide with Fluorescein Labeling Kit

The TRAP-6 hexapeptide was synthesized as previously described (Kaufmann R. ibid). Two (2) mg of the peptide were labeled and purified with the use of biotin labeling kit as described in example 12. Labeled peptide gave orange red powder. Spectroscopic analysis of the peptide gave new absorbance peak at O.D.=490 nm

Example 22

Use of Biotin-O-PFP for N-Terminus Labeling in Solid Phase Peptide Synthesis The MOG peptide 35-55 was synthesized according to the following method: First amino acid Fmoc-Lys(Boc)-OH was bound to Wang resin as described by Sieber et al., (Tetrahedron Let. Vol. 28, p. 6147, 1987). The peptide was synthesized by subsequent steps of coupling and deprotection. Coupling was preformed by HOBt/HBTU in DMF. Fmoc protecting group was removed by piperidine in DMF. By the end of the synthesis the Fmoc was removed the last amino acid (Met). The resin was incubated with 2 eq of Biotin-O-PFP for 2 h (hours) under nitrogen environment. Efficiency of biotin binding was estimated by Kaiser Test. The biotin labeled peptide was cleaved from the resin by 95% of TFA+ 2.5% water+2.5% EDT for 2 hours. The acid was evaporated in vacuum over KOH pellet. The labeled peptide was analyzed by HPLC and MS.

Example 23

Use of Biotin-O-PFP for Labeling on Side Chain Lysine in Solid Phase Peptide Synthesis The MOG peptide 35-55 was synthesized according to the following method: First amino acid Fmoc-Lys(Mtt)-OH was bound to Wang resin as described by Sieber et al., (Tetrahedron Let. Vol. 28, p. 6147, 1987). The peptide was synthesized by subsequent steps of coupling and deprotection. Coupling was preformed by HOBt/HBTU in DMF. Fmoc protecting group was removed by piperidine in DMF. After the coupling of the last amino acid, Mtt side chain protecting group of Lys was selectively removed by 1% TFA to expose the amino group of the Lys. The resin was incubated with 2 eq of Biotin-O-PFP for 2 h under nitrogen environment. Efficiency of biotin binding was estimated by Kaiser Test. By the end of the synthesis the Fmoc was removed and the biotin labeled peptide was cleaved from the resin by 95% of TFA+ 2.5% water+2.5% EDT for 2 hours. The acid was evaporated in vacuum over KOH pellet. The labeled peptide was analyzed by HPLC and MS.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation.

The means, materials, and steps for carrying out various disclosed chemical structures and functions may take a variety of alternative forms without departing from the invention. Thus any method step language, as may be found in the specification above and/or in the claims below, followed by a functional statement, are intended to define and cover whatever chemical structure, or whatever function, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

The invention claimed is:

1. A kit useful for the labeling of a biomolecule comprising:
   a) an activated labeling reagent having the formula selected from the group consisting of L-Ph and L-Sp-Ph, wherein L is an activated labeling molecule suitable for labeling of a biomolecule, Sp is a spacer molecule that links L to Ph, and Ph is a phenol, wherein L is selected from the group consisting of rhodamine, biotin, and fluorescein, Sp is 6-aminohexanoic acid, and Ph is pentafluoro-phenol;
   b) a reaction solution;
   c) a stop solution;
   d) a precipitation solution;
   e) a separation solution; and
   f) a separation gel,
   wherein the kit further comprises instructions for use.

2. The kit according to claim 1, wherein the biomolecule is selected from the group consisting of a protein, a peptide, a nucleic acid molecule, a sugar and a lipid.

3. The kit according to claim 1, wherein the biomolecule is a peptide or a protein.

4. A method for labeling a biomolecule comprising the steps of:
   (a) providing the kit according to claim 1;
   (b) exposing the biomolecule to the activated labeling reagent to provide a labeled biomolecule; and
   (c) precipitating the labeled biomolecule.

5. The kit according to claim 1, wherein L is rhodamine.

* * * * *

UNITED STATES PATENT AND TRADEMARK OFFICE
CERTIFICATE OF CORRECTION

| | | |
|---|---|---|
| PATENT NO. | : 8,435,800 B2 | Page 1 of 1 |
| APPLICATION NO. | : 11/719616 | |
| DATED | : May 7, 2013 | |
| INVENTOR(S) | : Gengrinovitch | |

It is certified that error appears in the above-identified patent and that said Letters Patent is hereby corrected as shown below:

On the Title Page:
Item [87] PCT Pub. Date, change "Mar. 26, 2006" to -- May 26, 2006 --.

Signed and Sealed this
Fourth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,435,800 B2  
APPLICATION NO.  : 11/719616  
DATED            : May 7, 2013  
INVENTOR(S)      : Stela Gengrinovitch Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1545 days.

Signed and Sealed this
Eighth Day of September, 2015

Michelle K. Lee
*Director of the United States Patent and Trademark Office*